United States Patent [19]

Kühle et al.

[11] 4,273,767
[45] Jun. 16, 1981

[54] COMBATING PLANT PESTS WITH PHOSPHORYLATED CARBAMOYL COMPOUNDS

[75] Inventors: Engelbert Kühle, Berg.-Gladbach; Hermann Hagemann, Cologne; Wolfgang Behrenz, Overath; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 110,585

[22] Filed: Jan. 9, 1980

[30] Foreign Application Priority Data

Jan. 31, 1979 [DE] Fed. Rep. of Germany ....... 2903592

[51] Int. Cl.$^3$ .................... A01N 9/40; C07F 57/20; C07F 57/22
[52] U.S. Cl. ................................ 424/211; 260/938
[58] Field of Search ....................... 260/938; 424/211

[56] References Cited

U.S. PATENT DOCUMENTS

| 3,069,312 | 12/1962 | Kohn | 260/938 |
| 3,183,258 | 5/1965 | Schuler et al. | 260/938 |

FOREIGN PATENT DOCUMENTS

| 1078370 | 3/1960 | Fed. Rep. of Germany . |
| 1193044 | 5/1965 | Fed. Rep. of Germany . |
| 1212967 | 3/1966 | Fed. Rep. of Germany . |
| 2038011 | 3/1971 | Fed. Rep. of Germany . |
| 935127 | 3/1964 | France . |

*Primary Examiner*—Anton H. Sutto
*Attorney, Agent, or Firm*—Sprung, Felfe, Horn, Lynch & Kramer

[57] ABSTRACT

A phosphorylated carbamoyl compound of the formula

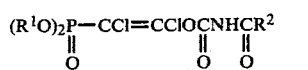

or

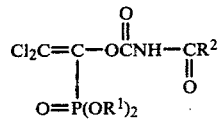

in which
$R^1$ represents a lower alkyl radical and
$R^2$ represents an optionally substituted alkoxy, cycloalkoxy, aralkoxy, aryloxy, alkylmercapto, cycloalkylmercapto, aralkylmercapto or arylmercapto radical, $NH_2$, an aliphatic, cycloaliphatic, araliphatic, aromatic or heterocyclic amine radical or an oximino radical, which possesses arthropodicidal and nematicidal properties.

10 Claims, No Drawings

COMBATING PLANT PESTS WITH PHOSPHORYLATED CARBAMOYL COMPOUNDS

The present invention relates to certain new phosphorylated carbamoyl compounds, to a process for their preparation and to their use as agents for combating pests, especially as insecticides.

It has already been disclosed that chlorine-containing organic phosphorus compounds have an insecticidal action. Thus, O,O-dimethyl-(1-hydroxy-2,2,2-trichloroethyl)-phosphoric acid ester (Trichlorfon) has been employed in practice in agriculture and in the hygiene sector for many years. However, this product is not always satisfactory with regard to its rate of action.

The present invention now provides, as new compounds, the phosphorylated carbamoyl compounds of the general formulae $$(R^1O)_2\underset{\underset{O}{\|}}{P}-CCl=CCl\underset{\underset{O}{\|}}{O}C\underset{\underset{O}{\|}}{N}HCR^2 \quad (Ia)$$

and $$Cl_2C=\underset{\underset{O=P(OR^1)_2}{|}}{C}-OC\underset{\underset{O}{\|}}{O}NHCOR^2 \quad (Ib)$$

in which
$R^1$ represents a lower alkyl radical, and
$R^2$ represents an optionally substituted alkoxy, cycloalkoxy, aralkoxy, aryloxy, alkylmercapto, cycloalkylmercapto, aralkylmercapto or arylmercapto radical, $NH_2$, an aliphatic, cycloaliphatic, araliphatic, aromatic or heterocyclic amine radical or an oximino radical.

Preferably, in formula (I), $R^1$ represents a $C_1$-$C_4$-alkyl radical and $R^2$ represents a saturated or unsaturated alkoxy radical with 1-6 C atoms (which can optionally be substituted by halogen, alkoxy, alkylthio or dialkylamino), a saturated or unsaturated cycloalkoxy radical with 5-7 C ring atoms (which can optionally be substituted by lower alkyl), an aralkoxy radical with 7-12 C atoms (which can optionally be substituted by halogen, nitro, alkyl, alkoxy or trihalogenomethyl), an aryloxy radical (which can optionally be substituted by halogen, nitro, alkyl, alkoxy, or trihalogenomethyl), an alkylmercapto, cycloalkylmercapto or aralkylmercapto radical (which can optionally be substituted by alkoxy, alkylmercapto or dialkylamino), an arylmercapto radical (which can optionally be substituted by halogen, nitro, alkyl or trihalogenomethyl), $NH_2$, a primary or secondary aliphatic, cycloaliphatic or araliphatic amine radical with 1-10 C atoms, an aryl amino radical (which can optionally be substituted by halogen, nitro, alkyl, alkoxy, trihalogenomethyl, trihalogenomethoxy or trihalogenomethylmercapto), a heterocyclic amine radical with 1-3 hetero-atoms or an oximino radical that is derived from an aliphatic, cycloaliphatic, araliphatic or aromatic oxime.

It is surprising that the compounds according to the invention have an activity as agents for combating pests, and especially an insecticidal activity, which is higher and starts more rapidly than the activity of the compounds mentioned as the state of the art. The new compounds thus represent an enrichment of the art.

The invention also provides a process for the preparation of a compound of the formula (Ia) or (Ib), in which a tetrachloroethoxycarbamoyl compound of the general formula $$Cl_3C-CHCl\underset{\underset{O}{\|}}{O}C\underset{\underset{O}{\|}}{N}HCR^2 \quad (II),$$

in which
$R^2$ has the meaning indicated above,
is reacted with a trialkyl phosphite of the general formula $$(R^1O)_3P \quad (III),$$

in which
$R^1$ has the meaning indicated above,
in the presence of a diluent.

When tetrachloroethoxycarbonyl carbamic acid methyl ester and trimethyl phosphite are used, the course of the reaction can be represented by the following equation:

$$Cl_3C-CCl\underset{\underset{O}{\|}}{H}O\underset{\underset{O}{\|}}{C}NHCOCH_3 \xrightarrow[\substack{-CH_3Cl; \\ -HCl}]{(CH_3O)_3P}$$

$$(CH_3O)_2\underset{\underset{O}{\|}}{P}CCl=CClOCONHCOOCH_3 +$$

$$Cl_2C=\underset{\underset{O=P(OCH_3)_2}{|}}{COCONHCOOCH_3}$$

The formula (II) provides a definition of the tetrachloroethoxycarbamoyl compounds to be used as the starting material. In this formula, $R^2$ preferably has the meanings stated above to be preferred in connection with the compounds of the formula (I).

The compounds of the formula (II) can be prepared by addition of appropriate hydroxy, mercapto, amino or oximino compounds onto tetrachloroethoxycarbonyl isocyanate, which is known (see Zh. Org. Khim 12, 1963 (1976)).

The trialkyl phosphites likewise required for the reaction are known, for example trimethyl phosphite, triethyl phosphite, tripropyl phosphite and triisopropyl phosphite.

Possible diluents are inert organic solvents. These include ethers, such as tetrahydrofuran and dioxane; hydrocarbons, such as benzene and toluene; and chlorinated hydrocarbons, such as tetrachloroethane and chlorobenzene.

The reaction is preferably carried out by heating the starting materials in the molar ratio 1:1 in a diluent at from 50° to 120° C., preferably from 80° to 120° C., alkyl chloride and hydrogen chloride being split off. When the evolution of gas has ended, the reaction is complete.

The reaction solution is worked up by distilling off the solvent, the remaining volatile constituents likewise being removed.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of the surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) or nematodes which comprises applying to the arthropods or nematodes, or to a habitat thereof, a compound of the present invention alone or in the form of a composition containing as active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds can be seen in the following illustrative example:

(a) Preparation of the starting materials of the formula (II) was effected as follows:

$$Cl_3C-CHClOCNHC-OCH_3$$
$$\phantom{Cl_3C-CHClOC}\|\phantom{NHC}\|$$
$$\phantom{Cl_3C-CHClOC}O\phantom{NHC}O$$

30 g of tetrachloroethoxycarbonyl isocyanate were dissolved in 100 ml of toluene, and 5 g of methanol were added dropwise. During this addition, the temperature rose to 35° C. The reaction solution was concentrated in vacuo and the residue was recrystallized from wash benzine. Melting point: 130°–131° C.; yield: 23 g (=68% of theory).

The following compounds were obtained in an analogous manner:

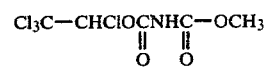
$$Cl_3C-CHClO-C-NHCOR^2$$
$$\phantom{Cl_3C-CHClO-}\|$$
$$\phantom{Cl_3C-CHClO-}O$$

| $R^2$ | Melting point, °C., or $(n_D^{20})$ |
|---|---|
| $-OC_2H_5$ | 88–89° |
| $-OC_2H_7i$ | 93–96° |
| $-OCH_2CH=CH_2$ | (1.5047) |
| $-OCH_2C\equiv CH$ | 133–134° |
| $-OCH_2CH_2OCH_3$ | (1.4991) |
| $-OCH_2CH_2SC_2H_5$ | 98° |
| $-O-C(CH_3)_2-CN$ | 120° |
| $-OCH_2-\langle\rangle$ | 116–117° |
| $-O-\langle\rangle$ | 147–149° |
| $-O-\langle\rangle-Cl$ (Cl) | 168° |
| $-OCH_2CH_2OC_3H_7-i$ | 90° |
| $-O-\langle H\rangle$ | 132–133° |
| $-O-CH_2-\langle H\rangle$ | 120–121° |
| $-OCH_2CH_2-\langle\rangle$ | 112–115° |
| $-OCH_2CH_2O-\langle\rangle$ | light coloured oil |
| $-OCH_2-\langle\rangle-O-\langle\rangle$ | (1.5700) |
| $-S-\langle\rangle$ | 156–157° |
| $-NHC_4H_9t$ | 130° |
| $-NH-\langle\rangle$ | 151–152° |

-continued $$Cl_3C-CHClO-\underset{\underset{O}{\|}}{C}-NHCOR^2$$

| $R^2$ | Melting point, °C., or $(n_D^{20})$ |
|---|---|
| —NH—(3,4-Cl₂-C₆H₃) 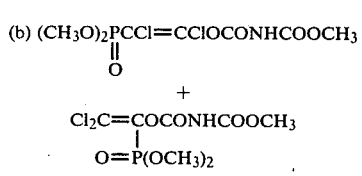 | 181° |
| —NH—C₆H₄—OCF₃ | 127–128° |
| —ON=C(CH₃)(SCH₃) | 136–137° |

(b) $(CH_3O)_2\underset{\underset{O}{\|}}{P}CCl=CClOCONHCOOCH_3$     (1)

$+$ $$Cl_2C=COCONHCOOCH_3$$
$$\underset{O=P(OCH_3)_2}{|}$$

8 g (1/30 mol) of N-(tetrachloroethoxycarbonyl)carbamic acid methyl ester were dissolved in 70 ml of toluene, and 5 g of trimethyl phosphite were added. The reaction solution was heated to 100° C., while stirring. Methyl chloride and hydrogen chloride were split off at this temperature. The mixture was kept at this temperature for 1 hour and heated to the reflux temperature for a short time. The solution was then concentrated in vacuo, whereupon 9 g of a colorless oil remained. $n_D^{20}$: 1.4682. Yield: quantitative.

Calculated: C 26.1% H 3.1% N 4.3% Cl 22.0%. Found: 25.3% 3.1% 3.9% 22.4%.

The following compound mixtures were obtained in an analogous manner:

$$(CH_3O)_2\underset{\underset{O}{\|}}{P}CCl=CClOCONHC-R^2 +$$
$$\underset{\underset{O}{\|}}{}$$

$$Cl_2C=COCONHCOR^2$$
$$\underset{O=P(OCH_3)_2}{|}$$

| Compound No. | $R^2$ | $n_D^{20}$ |
|---|---|---|
| 2 | —OC₂H₃ | 1.4694 |
| 3 | —OC₃H₇i | 1.4611 |
| 4 | —OCH₂CH=CH₂ | 1.4807 |
| 5 | —OCH₂C≡CH | 1.4813 |
| 6 | —OCH₂CH₂OCH₃ | 1.4712 |
| 7 | —OCH₂CH₂SC₂H₅ | 1.4827 |
| 8 | —OC(CH₃)₂CN | 1.4831 |
| 9 | —OCH₂—C₆H₅ | 1.5119 |
| 10 | —O—C₆H₅ | |
| 11 | —O—(2,4-Cl₂-C₆H₃) | 1.5240 |

-continued $$(CH_3O)_2\underset{\underset{O}{\|}}{P}CCl=CClOCONHC-R^2 +$$
$$\underset{\underset{O}{\|}}{}$$

$$Cl_2C=COCONHCOR^2$$
$$\underset{O=P(OCH_3)_2}{|}$$

| Compound No. | $R^2$ | $n_D^{20}$ |
|---|---|---|
| 12 | —S—C₆H₅ | 1.5430 |
| 13 | —NHC₄H₉t | 1.4802 |
| 14 | —NH—C₆H₅ | 1.5225 |
| 15 | —NH—(2,3-Cl₂-C₆H₃) | 1.5535 |
| 16 | —NH—C₆H₄—OCF₃ | 1.4997 |
| 17 | —ON=C(CH₃)(SCH₃) | 1.4912 |
| 18 | —OCH₂CH₂OC₃H₇i | 1.4665 |
| 19 | —O—C₆H₁₁ | 1.4858 |
| 20 | —OCH₂—C₆H₁₁ | 1.4845 |
| 21 | —OCH₂CH₂—C₆H₅ | 1.5148 |
| 22 | —OCH₂CH₂O—C₆H₅ | 1.5214 |
| 24 | —OCH₂—C₆H₄—O—C₆H₅ | 1.5396 |

EXAMPLE 2

$$(C_2H_5O)_2\underset{\underset{O}{\|}}{P}CCl=CClO\underset{\underset{O}{\|}}{C}NHC\underset{\underset{O}{\|}}{O}CH_3 \quad (23)$$

$+$ $$Cl_2C=COCONHCOCH_3$$
$$\underset{O=P(OC_2H_5)_2}{|}\quad\underset{O}{\|}$$

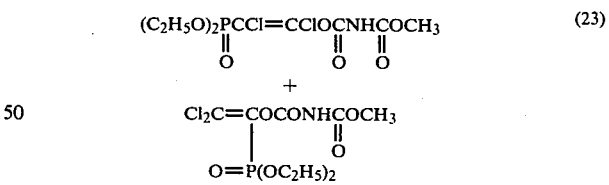

30 g of N-(tetrachloroethoxycarbonyl)carbamic acid methyl ester were heated to 100° C. for 5 hours, 19 g of triethyl phosphite in 120 ml of toluene being added. The mixture was concentrated in vacuo and 34 g (=93% of theory) of a light yellow oil, $n_D^{20}$: 1.4612, were obtained as the residue.

According to the NMR spectrum and thin layer chromatography, the reaction product consisted of the two isomers indicated.

Calculated: C 30.9% H 4.0% N 4.0% Cl 20.3%. Found: 30.9% 4.6% 4.0% 19.7%.

The pesticidal activity of the compounds of this invention is illustrated by the following biotest Examples. examples wherein the compounds according to the present invention are each identified by the number (given in brackets) from examples 1 and 2 hereinabove.

EXAMPLE 3

$LT_{100}$ test for Diptera
Test insects: *Musca domestica* resistant
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knockdown" was determined.

In this test, for example, the following compounds showed a superior action compared to the prior art: (1) to (17), (23) and (24).

EXAMPLE 4

$LT_{100}$ test for Diptera
Test insects: *Aedes aegypti*
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knockdown" was determined.

In this test, for example, the following compounds showed a superior action compared to the prior art: (1) to (16), (23) and (24).

EXAMPLE 5

$LD_{100}$ test
Test insects: *Sitophilus granarius*
Number of test insects: 25
Solvent: Acetone The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the tes insects was observed 3 days after the commencement of the experiments. The destruction, in %, was determined. 100% denoted that all of the test insects had been killed; 0% denoted that none of the test insects had been killed.

In this test, for example, the following compounds showed a superior action compared to the prior art: (1) to (17), (23) and (24).

EXAMPLE 6

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared to the prior art: (1), (2), (4), (5), (6), (7), (9), (14), (15), (17) and (24).

EXAMPLE 7

Test with *Lucilia cuprina* res. larvae
Solvent:
35 parts by weight of ethylene glycol monomethyl ether and
35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

About 20 *Lucilia cuprina* res. larvae were introduced into a test tube which contained approximately 1 cm³ of horse muscle and 0.5 ml of the preparation of active compound. After 24 hours, the degree of destruction in % was determined.

In this test, for example, the following compound showed a superior action compared to the prior art: (5).

EXAMPLE 8

Test with *Musca autumnalis*
Solvent:
35 parts by weight of ethylene glycol monomethyl ether
35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

10 *Musca autumnalis* adults were introduced into Petri dishes containing filter paper discs of appropriate size which had been saturated one day before the start of the experiment with 1 ml of the preparation of active compound to be tested. After 3 hours, the degree of destruction was determined.

In this test, for example, the following compounds showed a superior action compared to the prior art: (2), (3), (4), (5) and (9).

It will be appreciated that the instant specification and examples are set forth by way of illustration and not limitation, and that various modifications and changes may be made without departing from the spirit and scope of the present invention.

What is claimed is:

1. A phosphorylated carbamoyl compound of the formula

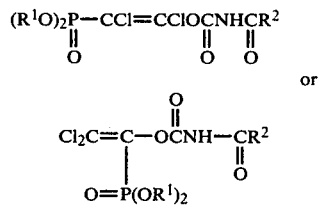

or in which
$R^1$ represents a lower alkyl radical and
$R^2$ represents an alkoxy radical with 1-6 C atoms (which can optionally be substituted by halogen, alkoxy, aryloxy, alkylthio or dialkylamino) an alkenoxy or alkynoxy radical with up to 6 C atoms, a cycloalkoxy radical with 5-7 C ring atoms (which can optionally be substituted by lower alkyl), an aralkoxy radical with 7-12 C atoms (which can optionally be substituted by halogen, nitro, akyl, alkoxy or trihalogenomethyl), an aryloxy radical (which can optionally be substituted by halogen, nitro, alkyl alkoxy or trihalogenomethyl), an alkylmercapto, cycloalkylmercapto or aralkylmercapto radical (which can optionally be substituted by alkoxy, alkylmercapto or dialkylamino), an arylmercapto radical (which can optionally be substituted by halogen, nitro, alkyl or trihalogenomethyl), $NH_2$, a primary or secondary aliphatic, cycloaliphatic or araliphatic amine radical with 1-10 C atoms, an aryl amino radical (which can optionally be substituted by halogen, nitro, alkyl, alkoxy, trihalogenomethyl, trihalogenomethoxy or trihalogenomethylmercapto), or an oximino radical that is derived from an aliphatic, cycloaliphatic, araliphatic or aromatic oxime.

2. A mixture of compounds of the two formulas according to claim 1.

3. A compound according to claim 1, in which $R^1$ is methyl and $R^2$ is methoxy.

4. A compound according to claim 1, in which $R^1$ is methyl and $R^2$ is isopropoxy.

5. A compound according to claim 1, in which $R^1$ is methyl and $R^2$ is phenoxy.

6. A compound according to claim 1, in which $R^1$ is methyl and $R^2$ is t-butylamino.

7. A compound according to claim 1, in which $R^1$ is methyl and $R^2$ is cyclohexylmethoxy.

8. An arthropodicidal or nematicidal composition containing as active ingredient an arthropodicidally or nematicidally effective amount of a compound according to claim 1 in admixture with a diluent.

9. A method of combating arthropods or nematodes which comprises applying to the arthropods or nematodes, or to a habitat thereof, an arthropodicidally or nematicidally effective amount of a compound according to claim 1.

10. The method according to claim 9, in which $R^1$ is methyl and $R^2$ is methoxy, isopropoxy, phenoxy, t-butylamino or cyclohexylmethoxy.

* * * * *